United States Patent [19]

Adams

[11] 4,037,021

[45] July 19, 1977

[54] PHOTOPOLYMERIZABLE COMPOSITIONS CONTAINING A KETO DIOXOLANE AS THE PHOTOSENSITIZER

[75] Inventor: William R. Adams, Oakland, N.J.

[73] Assignee: Sun Chemical Corporation, New York, N.Y.

[21] Appl. No.: 628,836

[22] Filed: Nov. 4, 1975

Related U.S. Application Data

[63] Continuation-in-part of Ser. No. 368,677, June 11, 1973, Pat. No. 3,944,509.

[51] Int. Cl.² .......................... C08F 2/46; C08F 4/00

[52] U.S. Cl. .................................. 428/522; 96/115 P; 260/340.9; 204/159.23; 427/44; 427/54; 428/35; 428/441; 428/451; 428/454; 428/461; 428/515

[58] Field of Search .............. 260/340.9; 204/159.23, 204/159.24; 96/115 P

[56] References Cited

U.S. PATENT DOCUMENTS

3,607,693   9/1971   Heine et al. ................... 204/159.15

*Primary Examiner*—Richard B. Turer
*Attorney, Agent, or Firm*—Cynthia Berlow

[57] ABSTRACT

Ethylenically unsaturated monomeric esters in the presence of keto-dioxolane compounds are photocured upon exposure to a source of radiation.

8 Claims, No Drawings

PHOTOPOLYMERIZABLE COMPOSITIONS CONTAINING A KETO DIOXOLANE AS THE PHOTOSENSITIZER

This application is a continuation-in-part of application Ser. No. 368,677, filed June 11, 1973 now U.S. Pat. No. 3,944,509, issued Mar. 16, 1976.

This invention relates to the use of keto-dioxolane compounds as photoinitiators for ethylenically unsaturated monomeric esters.

The use of photopolymerizable ethylenically unsaturated monomeric materials in coating compositions, printing inks, adhesives, and the like is known. It is also known that such monomeric materials are converted into polymers by the action of radiation and that they will polymerize at an improved rate when exposed to radiation in the presence of a photoinitiator.

It has now been found that polymers of ethylenically unsaturated monomeric esters having improved curing speeds can be obtained with no sacrifice of quality of the product by carrying out the photopolymerization in the presence of a novel keto-dioxolane compound.

The sensitizers of this invention have the following structure:

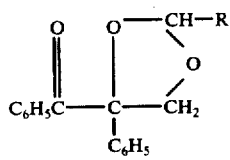

wherein R is alkyl of up to about nine carbon atoms, e.g., pentyl, octyl, or 2-ethylhexyl; alkyl of from one to about nine carbon atoms substituted with at least one halogen (chlorine, bromine, iodine, or fluorine), alkoxy, or the like; phenyl; phenyl substituted with at least one halogen, alkoxy, hydroxy, nitro, carboalkoxy, alkylamine, carboxyalkenyl wherein the alkenyl group has about two to six carbon atoms, or the like; heterocyclic group of about three to twelve ring-carbon atoms; or cycloalkyl of five to eight ring-carbon atoms.

Examples of such derivatives include, but are not limited to, 2-trichloromethyl-4-benzoyl-4-phenyl-1, 3-dioxolane; 2-(p-dimethylaminophenyl)-4-benzoyl-4-phenyl-1, 3-dioxolane; 2-cinnamyl-4-benzoyl-4-phenyl-1, 3-dioxolane; 2-furyl-4-benzoyl-4-phenyl-1, 3-dioxolane; and the like; and mixtures thereof.

The acyloin derivatives of this invention may be prepared by any known and convenient means, such as for example by the acid-catalyzed condensation of alpha-methylolbenzoin with an aliphatic or an aromatic aldehyde, e.g., p-dimethylaminobenzaldehyde, acetaldehyde, chloral, furfural, and the like.

These keto-dioxolane derivatives are effective initiators in the photopolymerization of a broad range of polymerizable ethylenically unsaturated monomeric compounds. Such a compound is generally a monomer or prepolymer, that is, a dimer, trimer, or other oligomer or mixture or copolymer thereof, generally described as the acrylic acid, methacrylic acid, itaconic acid, and the like, ester of an aliphatic polyhydric alcohol such as for example the di- and polyacrylates, the di- and polymethacrylates, and the di- and polyitaconates of ethylene glycol, triethylene glycol, tetraethylene glycol, tetramethylene glycol, trimethylolethane, trimethylolpropane, butanediol, pentaerythritol, dipentaerythritol, tripentaerythritol, other polypentaerythritols, sorbitol, d-mannitol, diols of unsaturated fatty acids, and the like.

Typical compounds include, but are not limited to, trimethylolpropane triacrylate, trimethylolethane triacrylate, trimethylolpropane trimethacrylate, trimethylolethane trimethacrylate, tetramethylene glycol dimethacrylate, ethylene glycol dimethacrylate, triethylene glycol dimethacrylate, tetraethylene glycol diacrylate, pentaerythritol diacrylate, pentaerythritol triacrylate, pentaerythritol tetraacrylate, dipentaerythritol diacrylate, dipentaerythritol triacrylate, dipentaerythritol tetraacrylate, dipentaerythritol pentaacrylate, dipentaerythritol hexacrylate, tripentaerythritol octoacrylate, pentaerythritol dimethacrylate, pentaerythritol trimethacrylate, dipentaerythritol dimethacrylate, dipentaerythritol tetramethacrylate, tripentaerythritol octamethacrylate, pentaerythritol diitaconate, dipentaerythritol transitaconate, dipentaerythritol pentaitaconate, dipentaerythritol hexaitaconate, ethylene glycol dimethacrylate, 1,3-butanediol diacrylate, 1,3-butanediol dimethacrylate, 1,4-butanediol diitaconate, sorbitol triacrylate, sorbitol tetraacrylate, sorbitol tetramethacrylate, sorbitol pentaacrylate, sorbitol hexacrylate, and the like, and modifications, mixtures, and prepolymers thereof.

Although the ratio of the amount of ester to the amount of photoinitiator may be about 10–99:1–90, it is generally about 90–99:1–10.

Commonly known modifiers may be incorporated into the formulations using these compositions, including plasticizers; wetting agents for the colorant, such as dichloromethylstearate and other chlorinated fatty esters; leveling agents, such as lanolin, paraffin waxes, and natural waxes; and the like. Such modifiers are generally used in amounts ranging up to about 3 percent by weight, preferably about 1 percent, based on the total weight of the formulation.

The formulations may be prepared in any known and convenient manner. Variables which determine the rate at which a photopolymerizable composition will dry include the nature of the substrate, the specific ingredients in the composition, the concentration of the photoinitiator, the thickness of the material, the nature and intensity of the radiation source and its distance from the material, the presence or absence of oxygen, and the temperature of the surrounding atmosphere. Irradiation may be accomplished by any one or a combination of a variety of methods. The composition may be exposed, for example, to actinic light from any source and of any type as long as it furnishes an effective amount of ultraviolet radiation, since the compositions activatable by actinic light generally exhibit their maximum sensitivity in the range of about 2000A. to 7000A., and preferably about 2000A. to 4000A.; gamma radiation emitters; and the like; and combinations of these. Suitable sources include, but are not limited to, carbon arcs, mercury vapor arcs, pulsed xenon lamps, fluorescent lamps with special ultraviolet light-emitting phosphors, argon glow lamps, photographic flood lamps, and so forth.

The time of irradiation must be sufficient to give the effective threshold dosage. Irradiation may be carried out at any convenient temperature, and most suitably is carried out at room temperature for practical reasons. Distances of the radiation source from the work may range from about 1 inch to 6 feet, and preferably about 5 inches to 4 feet.

When cured by radiation, the compositions are dry, flexible, abrasion resistant, and chemical resistant; also they have excellent ink receptivity, hydrophilic-hydrophobic balance, dot resolution, and initial roll-up, making them particularly suitable in such applications as presensitized lithographic printing plates and photoresists. The compositions are also useful as binders for magnetic tape; printing inks; adhesives for foils, films, papers, fabrics, and the like; coatings for metals, plastics, paper, wood, foils, textiles, glass cardboard, box board, and the like; markers for roads, parking lots, airfields, and similar surfaces, and so forth. Stock which may be printed includes paper, clay-coated paper, and box board. In addition, the compositions are suitable for the treatment of textiles, both natural and synthetic, e.g., in vehicles for textile printing inks or for specialized treatments of fabrics to produce water repellency, oil and stain resistance, crease resistance, etc.

When used as vehicles for inks, e.g., printing inks, the compositions may be pigmented with any of a variety of conventional organic or inorganic pigments, e.g., molybdate orange, titanium dioxide, lithol rubine red, diarylide yellow, chrome yellow, phthalocyanine blue, zinc oxide, and carbon black, as well as colored with dyes in a conventional amount. The vehicle may be used in an amount ranging from about 20 to 99.9 percent and the amount of colorant may range from about 0.1 to 80 percent of the weight of the total composition.

Typical laminations using the compositions of this invention as adhesives include polymer-coated cellophane to polypropylene, Mylar to a metal such as aluminum or copper, polypropylene to aluminum, and the like.

The compositions may also be utilized for metal coatings and particularly for metals which are to be subsequently printed. Glass and plastics may also be printed or coated, and the coatings are conventionally applied by roller or spray. Pigmented coating systems may be used for various polyester and vinyl films; glass; polymer-coated cellophane; treated and untreated polyethylene, for example in the form of disposable cups or bottles; treated and untreated polypropylene; and the like. Examples of metals which may be coated include sized and unsized tin plate.

Photopolymerizable elements prepared from these compositions comprise a support, e.g., a sheet or plate, having superimposed thereon a layer of the above-described photopolymerizable materials. Suitable base or support materials include metals, e.g., steel, aluminum, or copper, plates; sheets; and foils; and films or plates composed of various film-forming synthetic resins or high polymers. Fillers or reinforcing agents can be present in the synthetic resin or polymer bases. In addition, highly reflective bases may be treated to absorb ultraviolet light, or a light absorbtive layer can be transposed between the base and photopolymerizable layer.

Photopolymerizable elements can be made by exposing to radiation selected portions of the photopolymerizable layer thereof until addition polymerization is completed to the desired depth in the exposed portions. The unexposed portions of the layer are then removed, e.g., by the use of solvents which dissolve the monomer or prepolymer but not the polymer.

When used as printing inks, coating compositions, and adhesives, the compositions described herein are used without volatile solvents and possess many advantages over conventional oleoresinous and solvent-type inks and coatings. The substrate need not be pretreated or prepared in any way. The use of volatile solvents and the attendant health and fire hazards and odor are eliminated. The inks and coatings have excellent adhesion to the substrate after exposure to radiation. They have good gloss and rubresistance and withstand temperatures as high as about 150° C. and as low as about −20° C. The printed or coated sheets can be worked and further processed immediately after exposure to the energy source.

The invention and its advantages will be better understood with reference to the following illustrative examples, but it is not intended to be limited thereto. In the samples, the parts are given by weight unless otherwise specified. Unless otherwise indicated, when an ingredient is solid at room temperature, the mixture may be heated to melt the solid ingredient, but generally not above 100° C., or it may be used in a mixture with other liquid ingredients. The atmospheric and temperature conditions were ambient unless otherwise noted.

EXAMPLE 1

A mixture of 24.2 grams (0.1 mole) of α-methylolbenzoin, 14.9 grams (0.1 mole) of p-dimethylaminobenzaldehyde, and 1.0 grams of p-toluenesulfonic acid was dissolved into 125 ml. of toluene and placed into a Dean-Stark apparatus. The reaction mixture was refluxed for 8 hours, and the theoretical amount of water was collected.

The solution was cooled, washed with 5% sodium carbonate solution, separated, and dried. Concentration under reduced pressure gave 32.3 grams of product melting at 118°–120° C.

Recrystallization from ethanol gave 29.6 grams (79.5% yield) of 2-(p-dimethylaminophenyl)-4-benzoyl-4-phenyl-1,3-dioxolane (m.p. 128°–129° C.). The elemental analysis was as follows:

|  | C | H | N |
|---|---|---|---|
| Calculated: | 77.19 | 6.21 | 3.75 |
| Found: | 77.31 | 6.15 | 3.73 |

EXAMPLE 2

The procedure of Example 1 was repeated except that the starting materials were α-methylolbenzoin and chloral. The product was a 63% yield of 2-trichloromethyl-4-benzoyl-4-phenyl-1, 3-dioxolane, analyzed as follows:

|  | C | H | $C_l$ |
|---|---|---|---|
| Calculated: | 54.91 | 3.50 | 28.67 |
| Found: | 55.03 | 3.49 | 28.50 |

EXAMPLE 3

The procedure of Example 1 was repeated except that the starting materials were α-methylolbenzoin and cinnamaldehyde. The product, 2-cinnamyl-4-benzoyl-4-phenyl-1, 3-dioxolane, was obtained in a yield of 73% and analyzed as follows:

|  | C | H |
|---|---|---|
| Calculated: | 80.88 | 5.66 |
| Found: | 80.97 | 5.62 |

EXAMPLE 4

The procedure of Example 1 was repeated except that the starting materials were α-methylolbenzoin and furfural. The product, 2-furyl-4-benzoyl-4-phenyl-1, 3-dioxolane, was obtained in a yield of 78% and analyzed as follows:

|  | C | H |
|---|---|---|
| Calculated: | 74.99 | 5.03 |
| Found: | 74.56 | 5.07 |

EXAMPLE 5

A composition comprising 95 parts of isocyanate-modified pentaerythritol triacrylate and 5 parts of 2-(p-dimethylaminophenyl)-4-phenyl-1, 3-dioxolane was coated onto a glass slide at a wet-film thickness of 0.3 mil and irradiated at a distance of 1.5 inches from a 100-watt/inch ultraviolet lamp. The coating dried to a flexible abrasion-resistant film in 1.5 seconds.

EXAMPLE 6

A. The procedure of Example 5 was repeated with each of the following sensitizers instead of 2-(p-dimethylaminophenyl)-4-benzoyl-4-phenyl-1, 3-dioxolane:

TABLE I

| Sensitizer | Cure speed, seconds |
|---|---|
| none | 10.0 |
| 2-trichloromethyl-4-benzoyl-4-phenyl | 3.0 |
| 2-cinnamyl-4-benzoyl-4-phenyl-1, 3-dioxolane | 2.0 |
| 2-furyl-4-benzoyl-4-phenyl-1, 3-dioxolane | 2.0 |

B. For comparative purposes, sensitizers outside of the scope of this invention were tested in the same manner as above with the following results:

TABLE II

|  | Cure time, seconds |
|---|---|
| Benzoin | 15 |
| α-methylbenzoin | 6.0 |
| α-phenylbenzoin | 5.5 |
| α-benzylbenzoin | 7.5 |
| benzoin acetate | 11.5 |
| α-methylbenzoin ethyl ether | 12 |
| benzil | 11 |
| benzophenone | 25 |

Thus it can be seen that compositions containing the specific keto-dioxolane compounds of this invention (part A) cure considerably faster than comparable compositions containing related sensitizers that are not within the scope of this invention (part B).

EXAMPLE 7

The procedure of Example 5 was repeated with each of the following esters instead of isocyanate-modified pentaerythritol triacrylate. The results are tabulated below:

TABLE III

| Ester | Cure speed, seconds |
|---|---|
| pentaerythritol tetraacrylate | 2.1 |
| triethanolpropane trimethacrylate | 3.6 |
| ethylene glycol dimethacrylate | 7.0 |
| triethylene glycol diacrylate | 3.8 |
| 1,3-butanediol diacrylate | 5.0 |
| 1,4-butanediol diitaconate | 7.1 |
| sorbitol pentaacrylate | 4.3 |

EXAMPLE 8

A printing ink was prepared from the following:

|  | Parts by Weight |
|---|---|
| Product of Example 5 | 90 |
| Phthalocyanine green | 10 |

A glass bottle printed with this green ink was exposed to a 100-watt/inch ultraviolet lamp at a distance of 2 inches. The ink dried in 3.0 seconds. It had excellent adhesion to the glass and good grease- and rub-resistance.

EXAMPLE 9

The procedure of Example 8 was repeated with each of the following substrates instead of glass: clay-coated sulfite board, 32-pound coated paper, aluminum, and tin-free steel. The results were comparable.

EXAMPLE 10

A laminate was made of a film of polymer-coated cellophane and a film of oriented polypropylene with a mixture of the following ingredients between the two: 95 parts of trimethylolethane dimethacrylate and 5 parts of 2-trichloromethyl-4-benzoyl-4-phenyl-1, 3-dioxolane.

The laminate was exposed at a distance of 2.0 inches from a 100-watt/inch ultraviolet lamp. A tight bond was effected in 4.0 seconds.

EXAMPLE 11

The procedure of Example 10 was repeated with each of the following substrates: Saran-coated cellophane and Saran-coated cellophane, corona-discharge surface-treated polyethylene and coated cellophane, and polyvinylidene dichloride-coated polypropylene and Mylar.

The laminations were successful as evidenced by tear seals having bond strengths of at least 300 grams per inch.

EXAMPLE 12

The procedure of Examples 5-11 were repeated except that instead of being exposed to ultraviolet light the samples were passed on a conveyor belt beneath the beam of a Dynacote 300,000-volt linear electron accelerator at a speed and beam current so regulated as to produce a dose rate of 0.5 megarad.

These systems produced resinous materials of varying degrees of hardness in films from 0.5 to 20 mils thick having tacky surfaces.

EXAMPLE 13

The procedure of Examples 5-11 were repeated except that instead of being exposed to ultraviolet light the samples were exposed to a combination of ultraviolet light and electron beam radiation in a variety of arrangements: ultraviolet light, then electron beam; electron beam, then ultraviolet light; ultraviolet light before and after electron beam; electron beam before and after ultraviolet radiation; and simultaneous electron beam and ultraviolet light radiation. The results were comparable.

What is claimed is:

1. A photopolymerizable composition consisting essentially of about 10-99 parts of (a) an ethylenically unsaturated monomeric ester and about 1-90 parts of (b)

a photosensitizer selected from the group consisting of 2-trichloromethyl-4-benzoyl-4-phenyl-1,3-dioxolane, 2-(p-dimethylaminophenyl)-4-benzoyl-4-phenyl-1,3-dioxolane, 2-cinnamyl-4-benzoyl-4-phenyl-1,3-dioxolane, and 2-furyl-4-benzoyl-4-phenyl-1,3-dioxolane.

2. The composition of claim 1 wherein the ratio of the amount of ester (a) to sensitizer (b) is about 90–99:1–10.

3. A photopolymerizable printing ink comprising the composition of claim 1 and a colorant.

4. A photopolymerizable coating composition comprising the composition of claim 1.

5. A photopolymerizable adhesive comprising the composition of claim 1.

6. A photopolymerizable element comprising a support and a coating thereon of the composition of claim 1.

7. A method of producing polymeric material which comprises exposing to a source of radiation about 10–99 parts of an ethylenically unsaturated monomeric ester in the presence of about 1–90 parts of the photosensitizer of claim 1.

8. The method of claim 7 wherein the photosensitizer is employed in an amount within the range of about 1–10 percent, based on the total weight of the composition.

* * * * *